United States Patent [19]

Monteleone et al.

[11] Patent Number: 5,767,305

[45] Date of Patent: Jun. 16, 1998

[54] CYCLOPROPYL CARBOXYLIC ACID ESTERS AND USES THEREOF IN IMPARTING, AUGMENTING AND ENHANCING AROMAS

[75] Inventors: Michael G. Monteleone, Hazlet; Gail I. Malcolm, Red Bank; Marie R. Hanna, Hazlet; Marc D. Evans, South Orange, all of N.J.

[73] Assignee: International Flavors & Fragrances Inc., New York, N.Y.

[21] Appl. No.: 832,094

[22] Filed: Apr. 3, 1997

[51] Int. Cl.[6] .................................................. C07C 69/74
[52] U.S. Cl. ................................. 560/124; 512/8; 512/22
[58] Field of Search ........................... 560/124; 512/8, 512/22

[56] References Cited

U.S. PATENT DOCUMENTS

| | | | |
|---|---|---|---|
| 3,925,460 | 12/1975 | Henrick et al. | 260/468 H |
| 3,926,860 | 12/1975 | Chappell | 560/124 |
| 4,406,829 | 9/1983 | Martel | 560/124 |
| 4,415,756 | 11/1983 | Demuth | 560/124 |
| 4,431,576 | 2/1984 | Martel | 560/124 |
| 4,536,330 | 8/1985 | Boden et al. | 252/522 R |

OTHER PUBLICATIONS

Henrick, et al, II, *J. Agric. Food Chem.*, vol. 24, No. 5, 1976, pp. 1023–1029, entitled "Ovicidal Activity and Its Relation to Chemical Structure for the Two–Spotted Spider Mite (*Tetranychus urticae* Koch) in a New Class of Miticides Containing the Cyclopropyl Group".

*Primary Examiner*—Michael L. Shippen
*Attorney, Agent, or Firm*—Arthur L. Liberman

[57] ABSTRACT

Described are cyclopropyl carboxylic acid esters defined according to the structure:

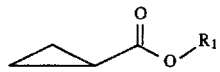

or the structure:

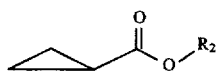

wherein $R_1$ is cis-3-hexenyl or cyclohexyl methyl and $R_2$ is one of n-hexyl, cis-3-hexenyl, cyclohexyl methyl or n-heptyl and uses thereof in augmenting, enhancing or imparting aromas in or to perfume compositions, colognes and perfumed articles. The compounds having the structure:

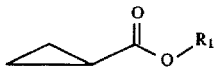

are novel compounds.

14 Claims, 13 Drawing Sheets

GLC PROFILE FOR EXAMPLE I, CRUDE.

FIG.2 NMR SPECTRUM FOR EXAMPLE I.

GLC PROFILE FOR EXAMPLE II.

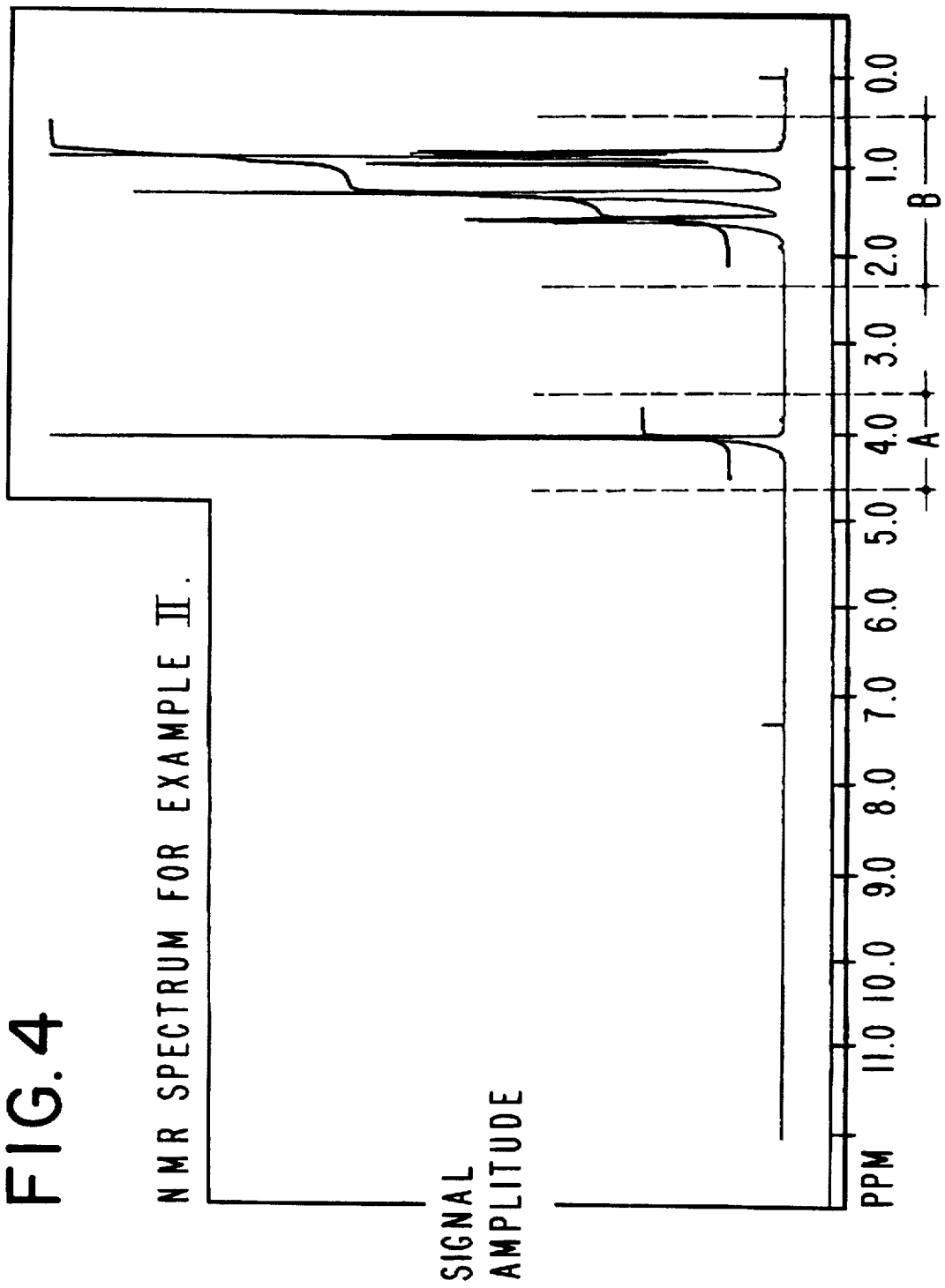

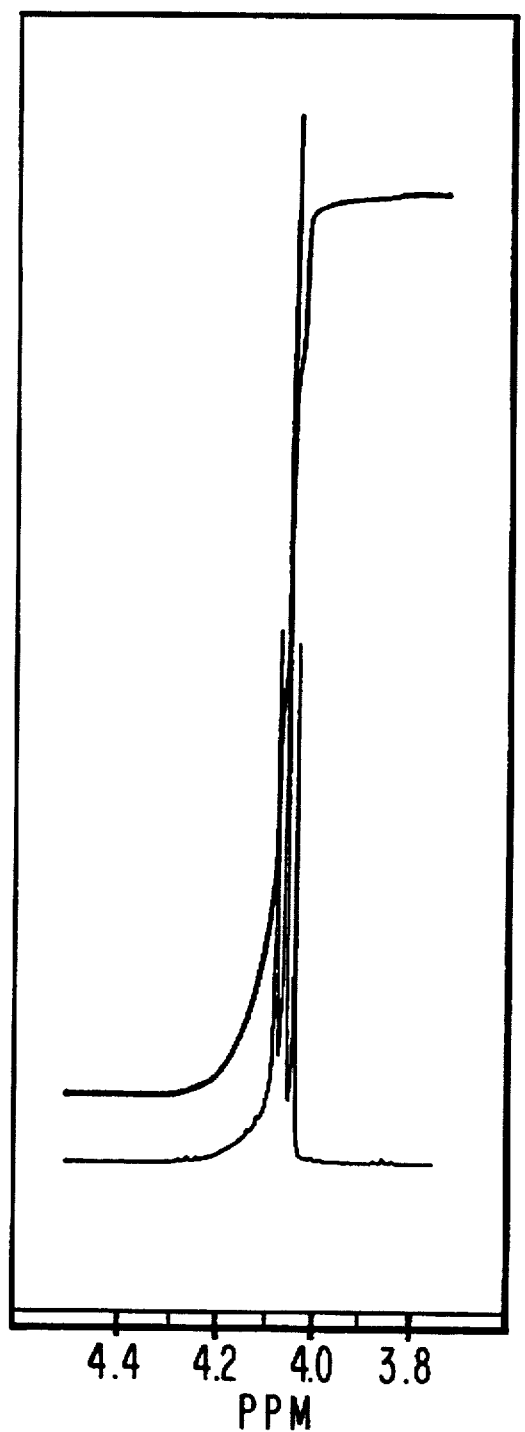
FIG.4-A

FIG.4-B
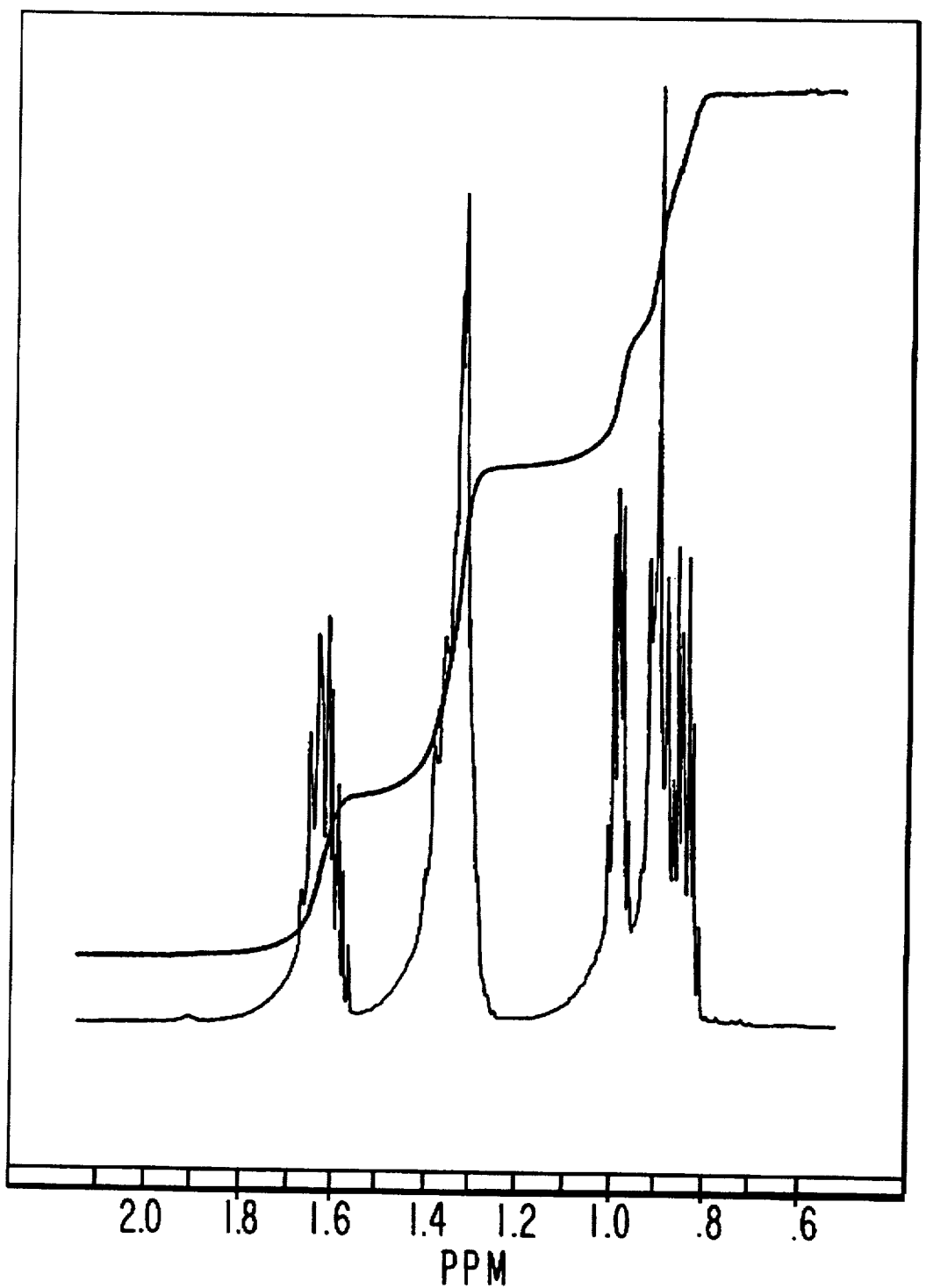

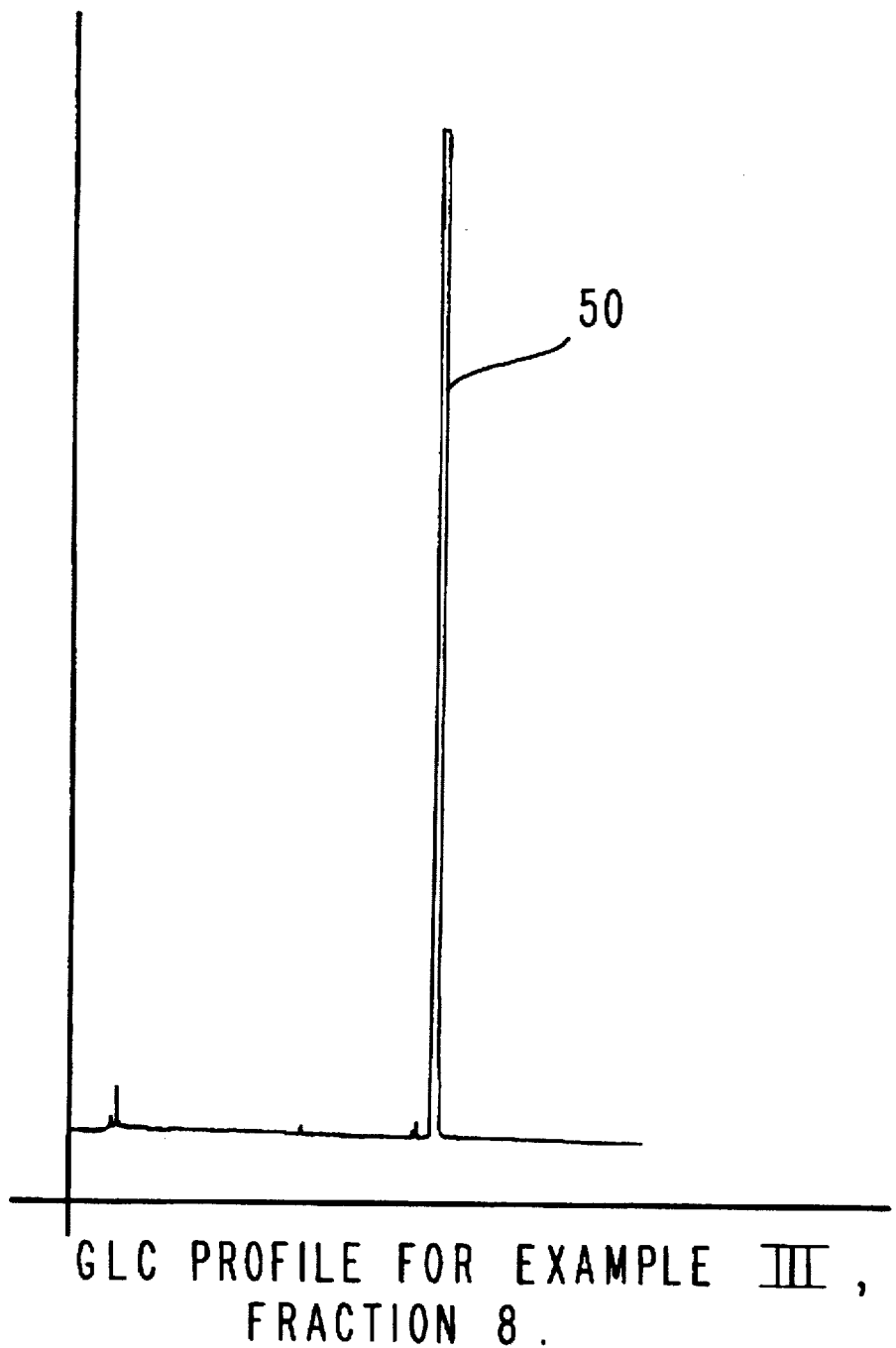

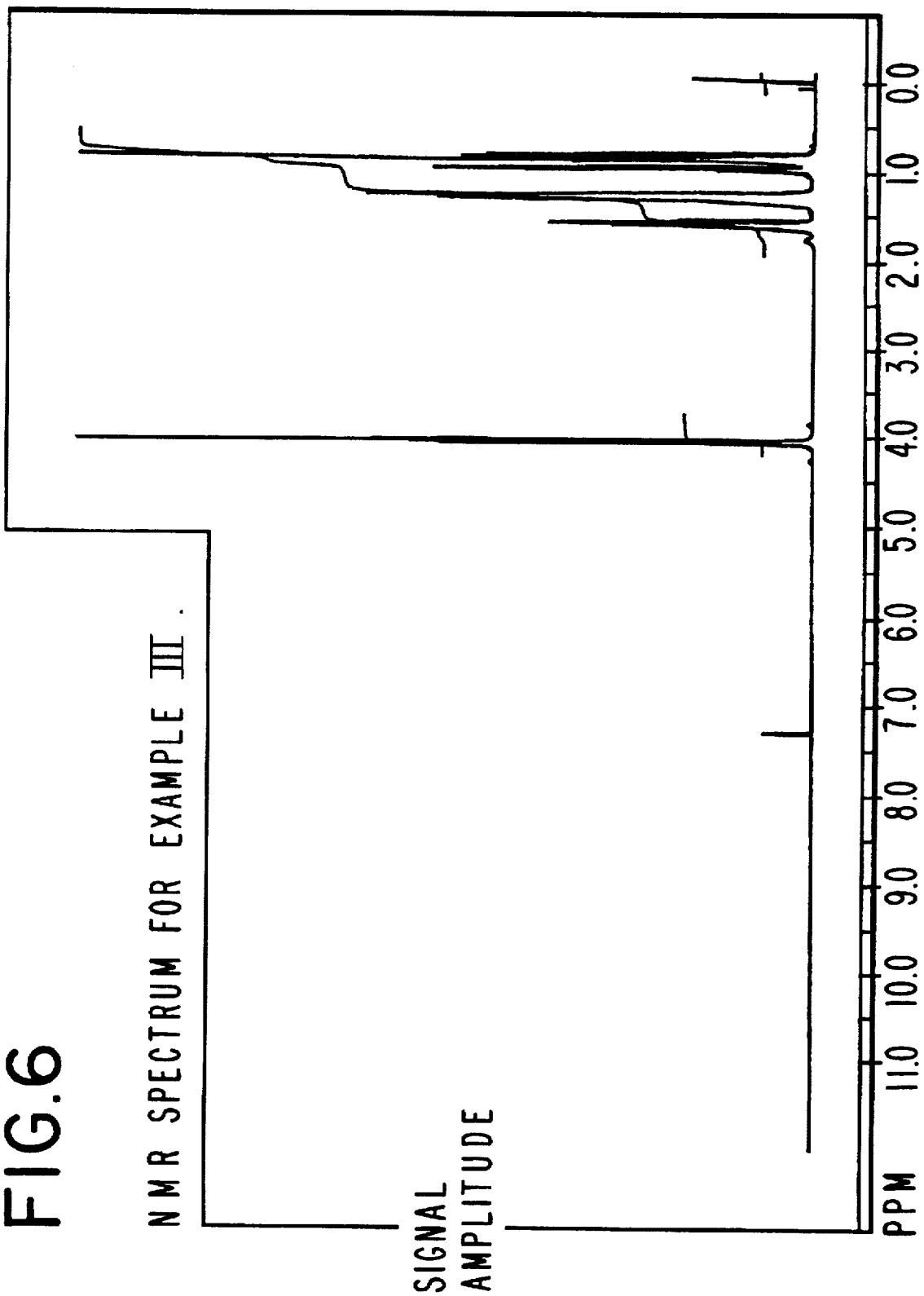

GLC PROFILE FOR EXAMPLE IV, CRUDE

NMR SPECTRUM FOR EXAMPLE IV, FRACTION 8.

FIG.8-A
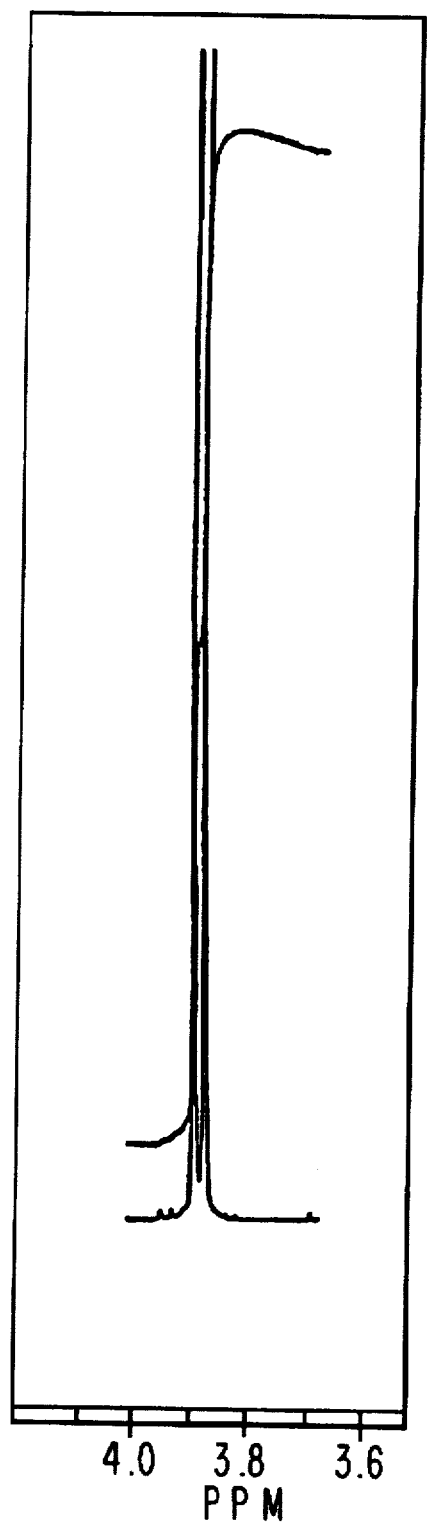

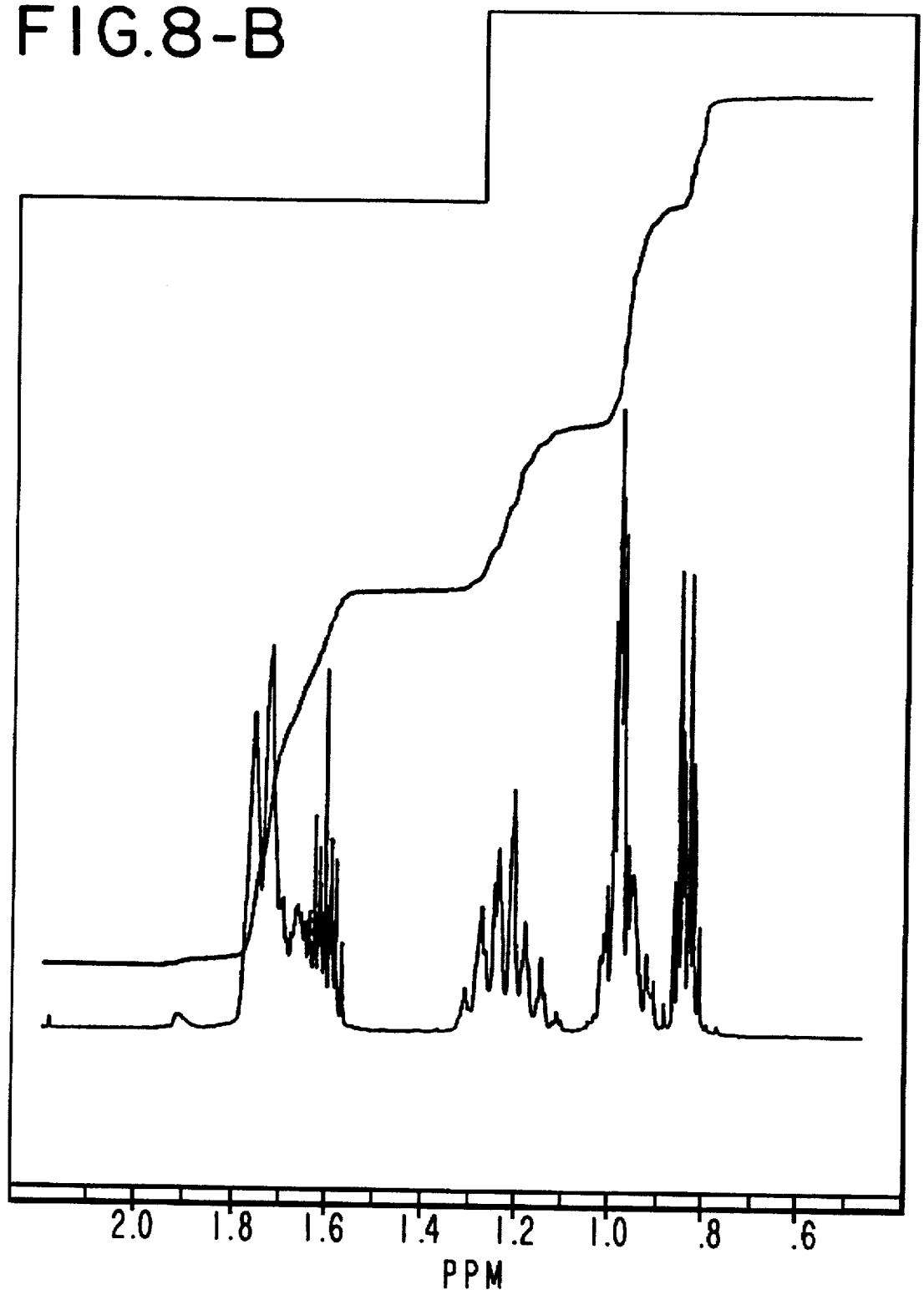
FIG. 8-B

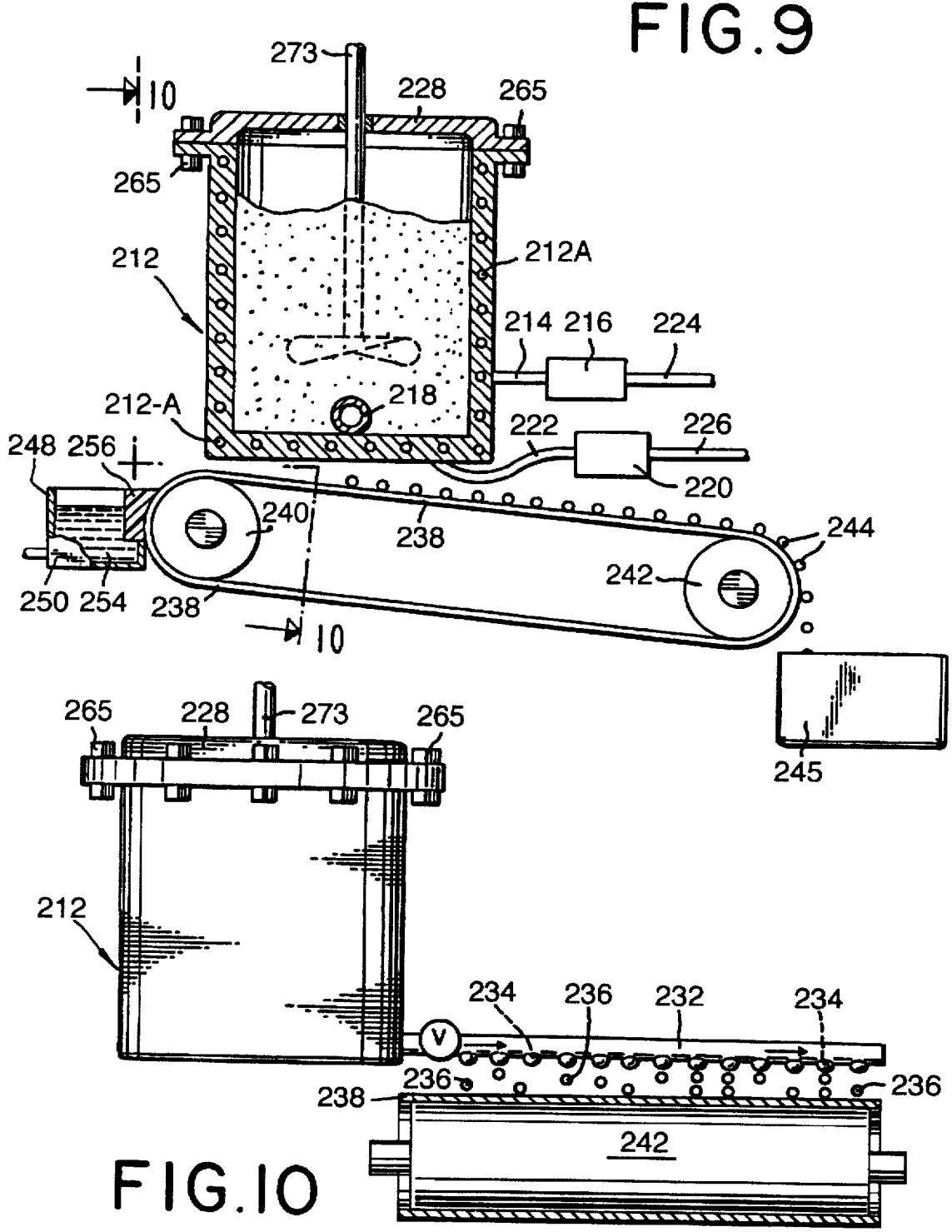

CYCLOPROPYL CARBOXYLIC ACID ESTERS AND USES THEREOF IN IMPARTING, AUGMENTING AND ENHANCING AROMAS

BACKGROUND OF THE INVENTION

The instant invention relates to cyclopropyl carboxylic acid esters defined according to the structure:

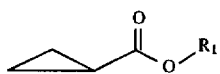

or the structure:

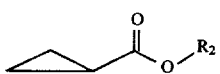

wherein $R_1$ is cis-3-hexenyl or cyclohexyl methyl and $R_2$ is n-hexyl, cis-3-hexenyl, cyclohexyl methyl or n-heptyl and uses of same in augmenting, enhancing or imparting an aroma in or to perfume compositions, colognes and perfumed articles.

Inexpensive chemical compounds which are substantive and long lasting and which can provide herbaceous, "rain forest", green, onion, garlic, almond, anisic, fruity, cherry, apple, pear, woody, mahogany and cigar box aromas with green, fruity, apple, almond, cherry, anisic, lilac, hyacinth, woody and amber topnotes are highly desirable in the art of perfumery. Many of the natural materials which provide such fragrances and contribute such desired nuances to perfume compositions as well as perfumed articles are high in cost, unobtainable at times, vary in quality from one batch to another and/or are generally subject to the usual variations of natural products.

There is, accordingly, a continuous effort to find synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the compositions.

Of particular importance are odorants of the muguet type in perfumery as well as the "woody cologne" type in perfumery.

Cyclopropyl moiety-containing materials are well known in the art of perfumery. Thus, compounds having the generic structure:

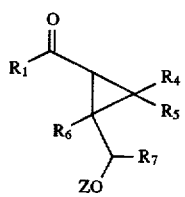

wherein $R_1$, $R_2$ and $R_3$ represent $C_1$–$C_{10}$ alkyl; Z is hydrogen; acyl having the structure:

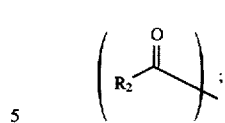

or substituted oxyacyl having the structure:

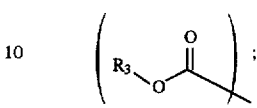

and wherein $R_4$, $R_5$, $R_6$ and $R_7$ represent hydrogen or $C_1$–$C_3$ lower alkyl are disclosed in U.S. Pat. No. 4,536,330 issued on Aug. 20, 1985 for their perfumery uses.

Cyclopropyl esters are known in the prior art, but their uses in perfumery have never been disclosed. Thus, compounds having the generic structure:

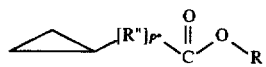

wherein p" is zero or 1; R" represents the moiety:

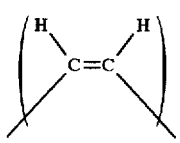

or the moiety:

N is 1, 2, 3 or 4; and R is alkyl of at least 10 carbon atoms, alkenyl of at least 10 carbon atoms or cycloalkyl, optionally substituted by one or more lower alkyl groups, is disclosed in U.S. Pat. No. 3,925,460 issued on Dec. 9, 1975, for the control of mites and ticks. Furthermore, U.S. Pat. No. 3,925,460 issued on Dec. 9, 1975 discloses, for use in the control of mites and ticks, compounds of the genus having the structure:

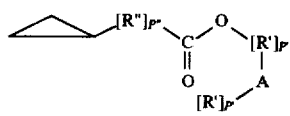

wherein p" and R" are defined, supra; R' represents, inter alia, alkenylene of 2–6 carbon atoms; p' is zero or 1; and A is alkenylene of 2–20 carbon atoms. However, U.S. Pat. No. 3,925,460 does not specifically disclose the compound having the structure:

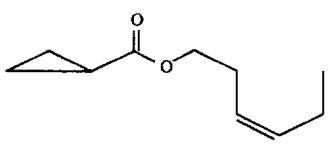

or having the structure:

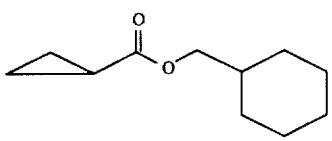

nor does said U.S. Pat. No. 3,925,460 disclose compounds even remotely similar to such compounds of our invention.

Henrick, et al. *J. Agric. Food Chem.*, Volume 24, No. 5 (1976) discloses, as miticides, compounds having the structures:

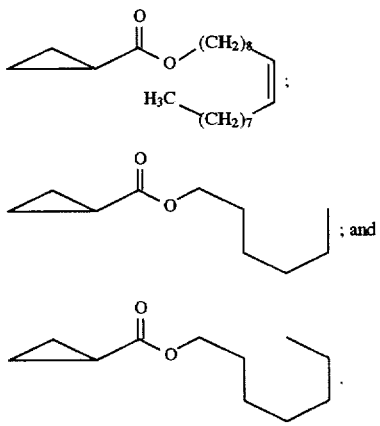

Nothing in the prior art, however, discloses the compounds of our invention, defined according to the structure:

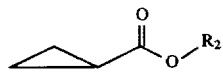

wherein $R_2$ is n-hexyl, cis-3-hexenyl, cyclohexyl methyl or n-heptyl for use in perfumery. Furthermore, nothing in the prior art specifically discloses the compounds having the genus:

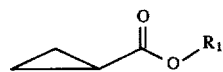

wherein $R_1$ is cis-3-hexenyl or cyclohexyl methyl; although the genus of compounds having the structure:

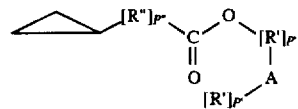

of U.S. Pat. No. 3,925,460 cited, supra, could, if proper selection were made from the many thousands of compounds covered in that genus, cover the compound having the structure:

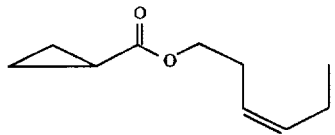

However, the compound having the structure:

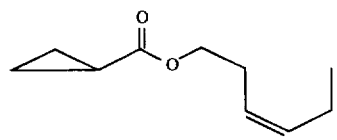

as well as the other cyclopropyl carboxylic acid esters of our invention have unexpected, unobvious and advantageous properties with respect to use in perfumery when compared to any of the other compounds of the genuses disclosed in the prior art.

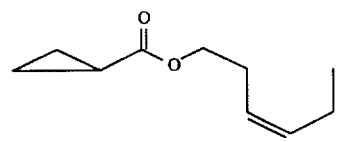

(conditions: 50 meter×0.32 mm methyl, 50 meter×0.32 mm methyl silicon column programmed from 75° up to 225° C. at 2° C. per minute).

Figure 2:
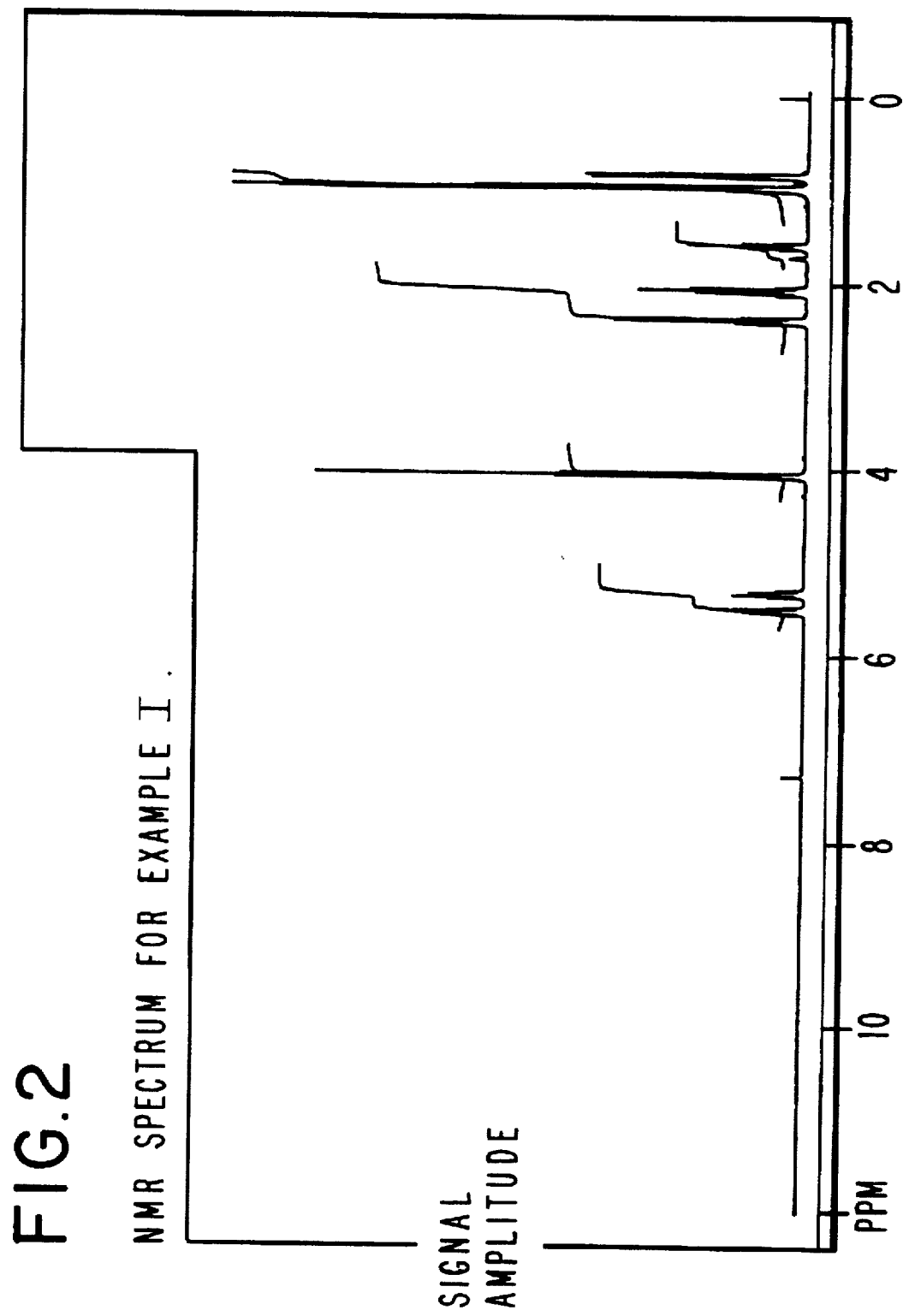

FIG. 2 is the NMR spectrum for bulked distillation fractions 8–22 of the distillation of the reaction product of Example I containing the compound having the structure:

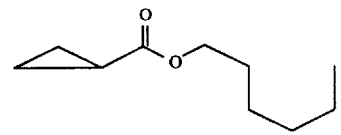

Figure 3:
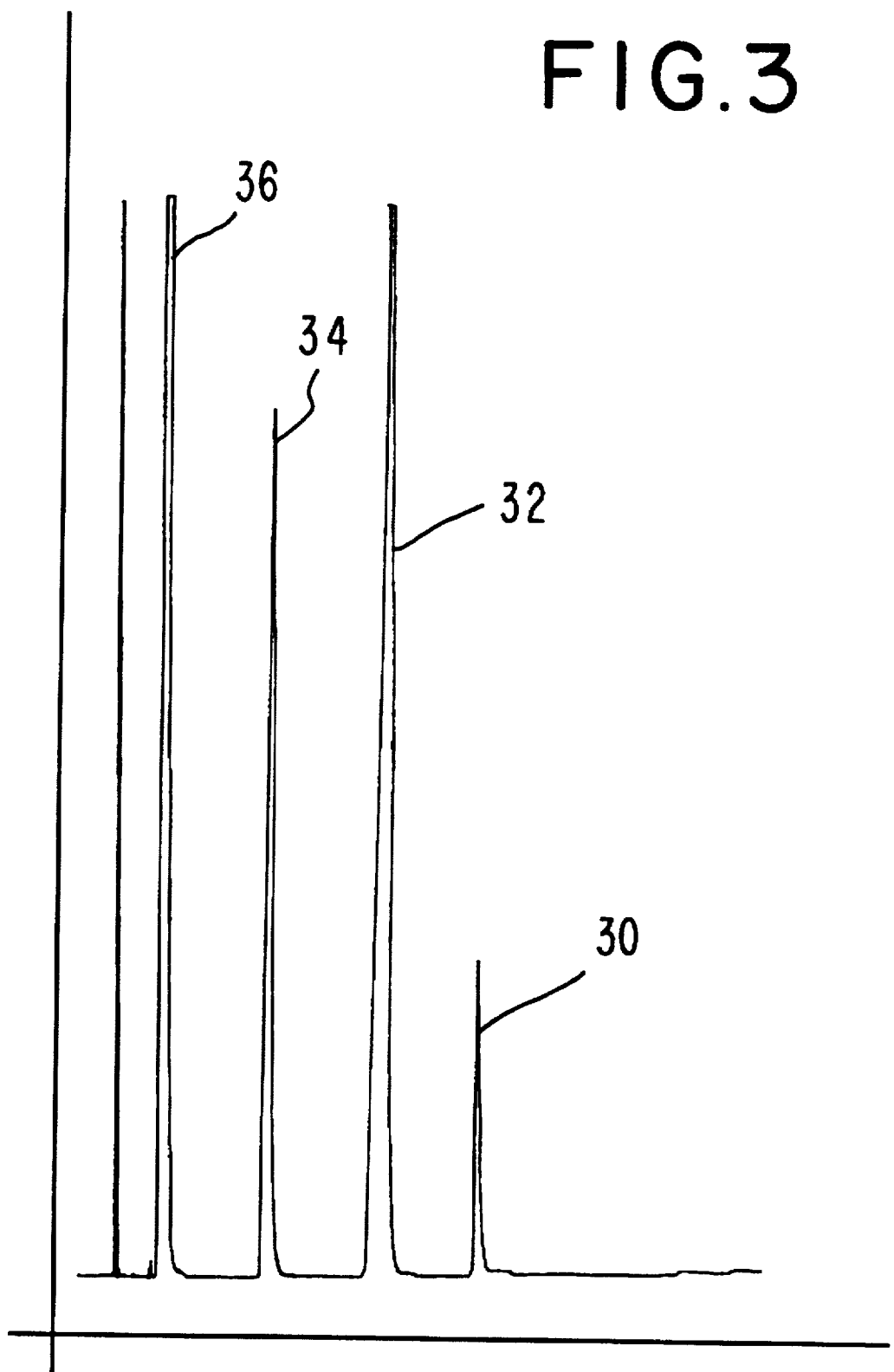

FIG. 3 is the GLC profile for the crude reaction product of Example II containing the compound having the structure:

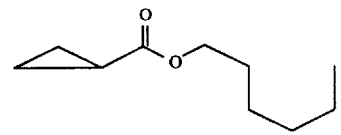

(conditions: CARBOWAX® column programmed from 80°–220° C. at 8° C. per minute).

FIG. 4 is the NMR spectrum for the compound having the structure:

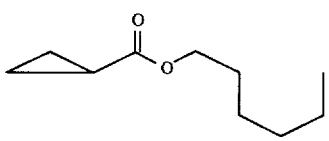

prepared according to Example II.

FIG. 4A is an enlargement of section "A" of the NMR spectrum of FIG. 4.

FIG. 4B is an enlargement of section "B" of the NMR spectrum of FIG. 4.

FIG. 5 is the GLC profile for fraction 8 of the distillation of the reaction product of Example III containing the compound having the structure:

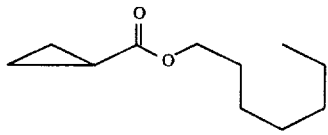

(conditions: SE-30 column programmed from 100°–220° C. at 8° C. per minute).

FIG. 6 is the NMR spectrum for the compound having the structure:

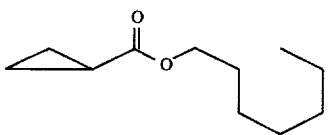

prepared according to Example III.

Figure 7:
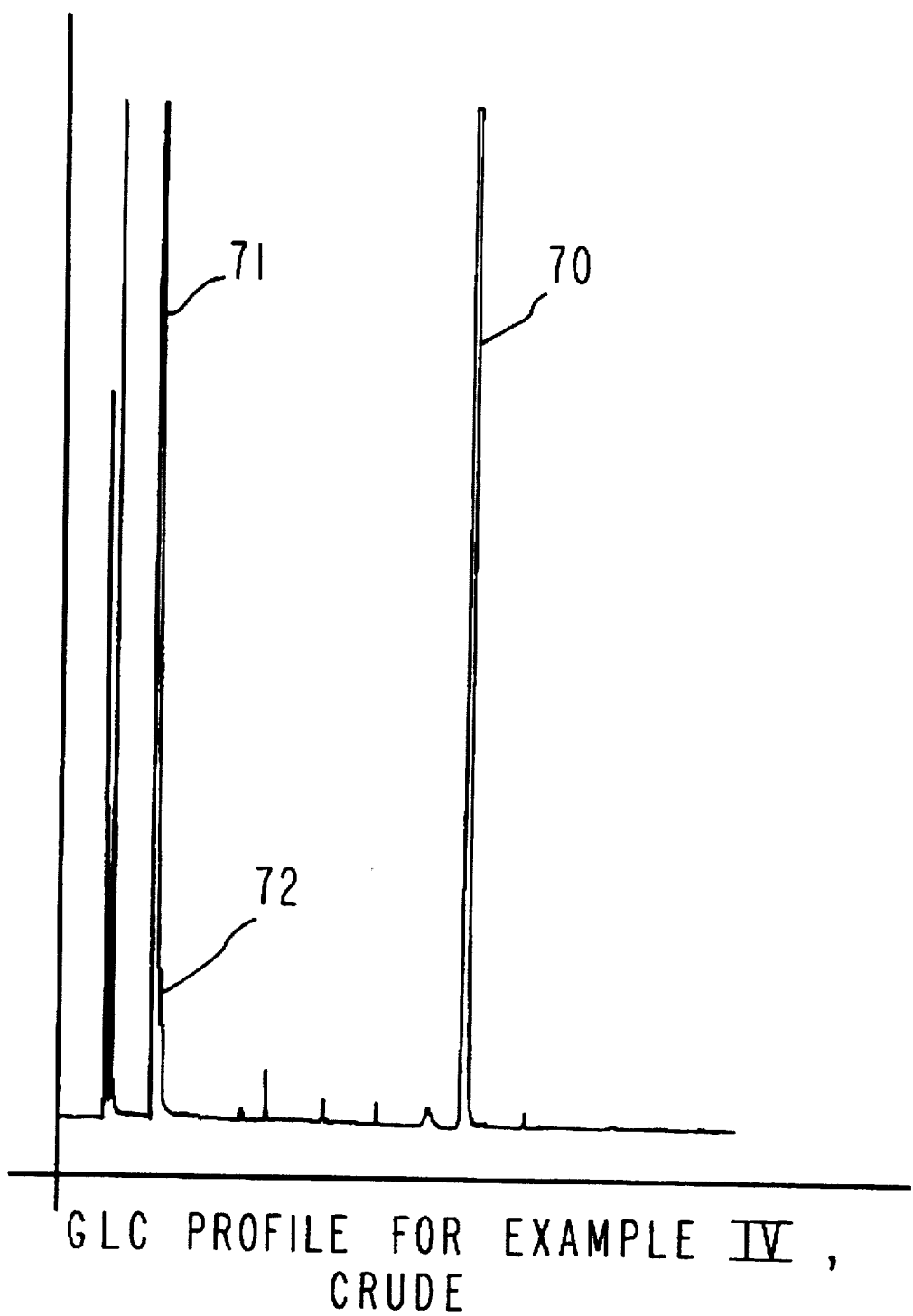

FIG. 7 is the GLC profile for the crude reaction product prepared according to Example IV having the structure:

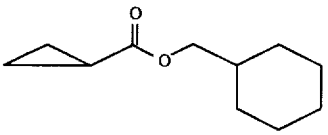

(conditions: CARBOWAX® column programmed from 100°–220° C. at 8° C. per minute).

Figure 8:
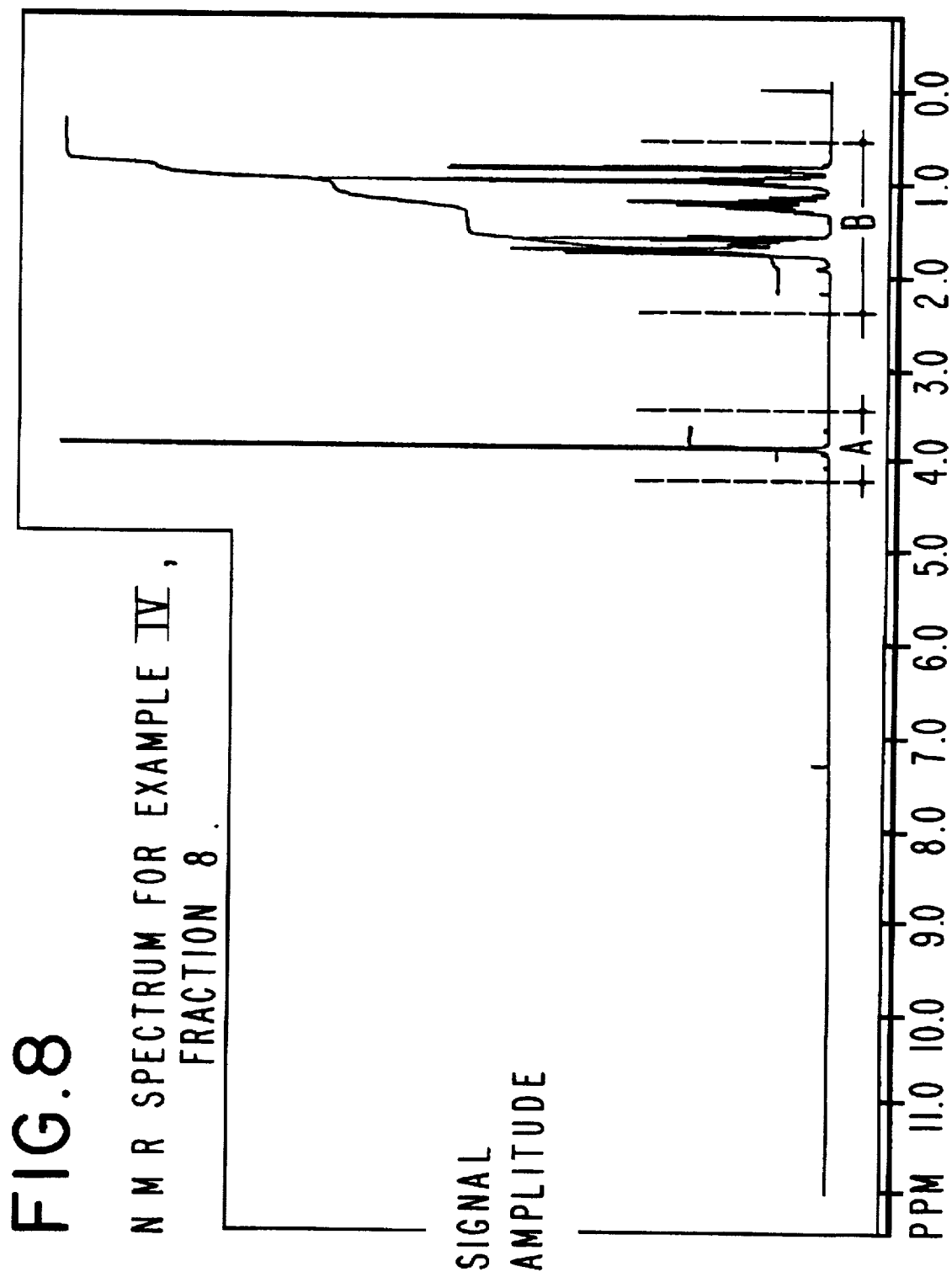

FIG. 8 is the NMR spectrum for fraction 8 of the distillation of the reaction product of Example IV for the compound having the structure:

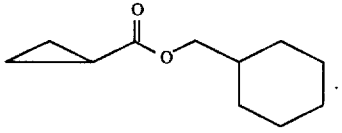

FIG. 8A is an enlargement of section "A" of the NMR spectrum of FIG. 8.

FIG. 8B is an enlargement of section "B" of the NMR spectrum of FIG. 8.

FIG. 9 is a partial side elevation view and partial sectional view of an apparatus for forming polymer pellets containing at least one of the cyclopropyl carboxylic acid esters of our invention.

FIG. 10 is a section taken along line 10—10 of FIG. 9.

DETAILED DESCRIPTION OF THE DRAWINGS

Figure 1:
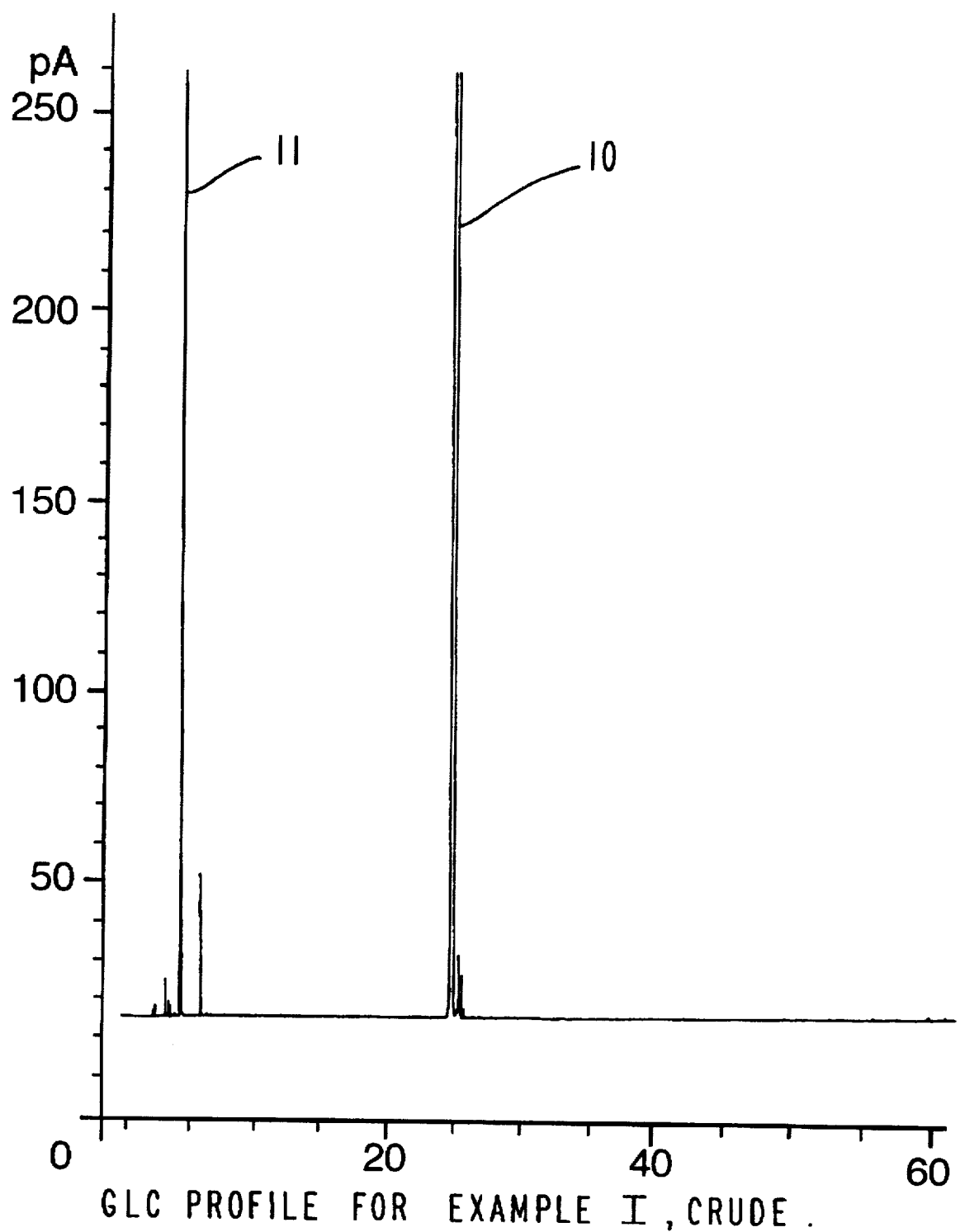
FIG. 1 is the GLC profile for the crude reaction product of Example I containing the compound having the structure.

Referring to FIG. 1, FIG. 1 is the GLC profile for the reaction product of Example I containing the compound having the structure:

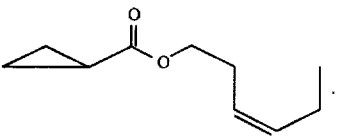

The peak indicated by reference numeral 10 is the peak for the compound having the structure:

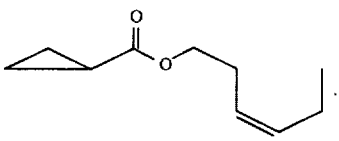

The peak indicated by reference numeral 11 is for the reaction solvent, toluene.

Referring to FIG. 3, FIG. 3 is the GLC profile for the crude reaction product of Example II containing the compound having the structure:

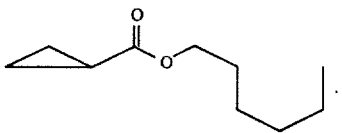

The peak indicated by reference numeral 30 is the peak for the reactant having the structure:

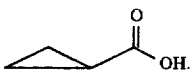

The peak indicated by reference numeral 32 is for the compound having the structure:

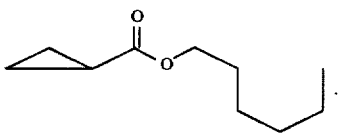

The peak indicated by reference numeral 34 is the peak for n-hexanol. The peak indicated by reference numeral 36 is for the reaction solvent, toluene.

Referring to FIG. 5, FIG. 5 is the GLC profile for fraction 8 of the distillation of the reaction product of Example III. The peak indicated by reference numeral 50 is the peak for the compound having the structure:

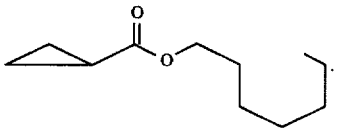

Referring to FIG. 7, FIG. 7 is the GLC profile for the crude reaction product of Example IV containing the compound having the structure:

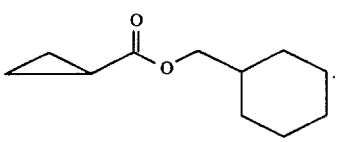

The peak indicated by reference numeral 70 is the peak for the compound having the structure:

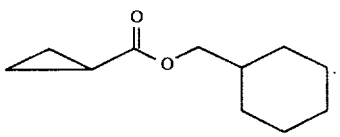

The peak indicated by reference numeral 72 is the peak for the reactant having the structure:

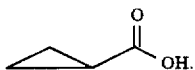

The peak indicated by reference numeral 71 is for the reaction solvent, toluene.

Referring to FIGS. 9 and 10, the apparatus used in producing polymeric fragrances containing one or more of the cyclopropyl carboxylic acid esters of our invention comprises a device for forming scented polyolefin (for example) pellets, which comprises a vat or container 212 into which a mixture of polyolefin such as polyethylene and an aromatic substance or scented material is placed (in this case, at least one of the cyclopropyl carboxylic acid esters of our invention).

The container is closed by an air-tight lid 228 and the air-tight lid 228 is clamped to the container 212 by bolts 265.

A stirrer 273 traverses the lid or cover 228 in an air-tight manner and is rotated in a suitable manner.

Container 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 saybolt seconds and having a melting point in the range of 200°–280° F. The heater 212A is operated to maintain the upper portion of the container 212 within a temperature range of from 250°–350° F. The bottom portion of the container is heated by means of heating coils 212A heated through control 220 connected thereto through a connecting wire 222 to maintain the lower portion of the container within a temperature range of from 250°–350° F.

Thus, polymer (e.g., polyethylene) is added to container 212 and is heated from 10–12 hours whereafter a scented aroma imparting material (at least one of the cyclopropyl carboxylic acid esters our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5–30% by weight of the scented material (containing at least one of the cyclopropyl carboxylic acid esters of our invention) are added to the polyolefin.

After the scent imparting material (e.g., a composition containing at least one of the cyclopropyl carboxylic acid esters of our invention) is added to the container 212, the mixture is stirred for a few minutes, for example, 5–15 minutes, and maintained within the temperature range as indicated, supra, by means of heating coils 212A.

The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter, the valve "V" is opened permitting the mass to flow outwardly through conduit 218/232 having a multiplicity of orifices 234, adjacent to the lower side thereof. The outer end of the conduit 218/232 is closed so that the liquid polymer (e.g., polyolefin) and aroma imparting material (e.g., a mixture containing at least one of the cyclopropyl carboxylic acid esters of our invention) will continuously drop through orifices 234 downwardly from conduit 232. During this time, the temperature of the polymer (e.g., polyolefin) and aroma imparting material (e.g., a mixture containing at least one of the cyclopropyl carboxylic acid esters of our invention) is accurately controlled so that a temperature in the range of from about 210°–275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the cyclopropyl carboxylic acid esters of our invention) mixture through the orifices 234 at a rate which will insure the formation of droplets 236 which will fall downwardly onto a moving conveyor belt 238 caused to run between conveyor wheels 240 and 242.

When the droplets 236 fall onto the conveyor 238, they form pellets 244 which harden almost instantaneously and fall off the end of the conveyor 238 into a container 245 and utilized in processes as illustrated, infra.

A feature of this aspect of the process of our invention is the provision for moistening the conveyor belt 238 to insure rapid formation of the solid polymeric (e.g., polyolefin) scented pellets 244 without sticking to the belt. The belt 238 is advantageously fabricated of a material which will not normally stick to a melted plastic, but a moistening means 248 insures a sufficiently cold temperature of the belt surface for an adequate formation of the pellets 244. The adequate moistening means comprises a container 250 which is continuously fed with water 254 to maintain a level for moistening a sponge element 256 which bears against the exterior of the belt 238.

THE INVENTION

The present invention provides cyclopropyl carboxylic acid esters defined according to the generic structures:

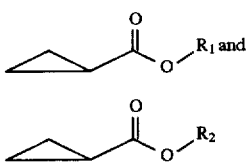

wherein $R_1$ is cis-3-hexenyl or cyclohexyl methyl and wherein $R_2$ is n-hexyl, cis-3-hexenyl, cyclohexyl methyl or n-heptyl as well as processes for utilizing such cyclopropyl carboxylic acid esters in perfumery. The compounds defined according to the generic structure:

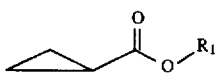

are novel compounds.

The compositions of matter of our invention produced according to the processes disclosed in the instant specification are capable of augmenting, enhancing or providing strong, persistent, herbaceous, "rain forest", green, onion, garlic, almond, anisic, fruity, cherry, apple, pear, woody, mahogany and cigar box aromas with green, fruity, apple, almond, cherry, anisic, lilac, hyacinth, woody and amber topnotes to perfume compositions, colognes and perfumed articles (e.g., solid or liquid, anionic, cationic, nonionic or zwitterionic detergents, fabric softener articles, drier-added fabric softener articles, fabric softener compositions, cosmetic powders, hair preparations, perfumed polymers and the like).

A number of the cyclopropyl carboxylic acid esters of our invention are known in the prior art, and two of the cyclopropyl carboxylic acid esters of our invention are novel as stated, supra, but the perfumery uses of all of the cyclopropyl carboxylic acid esters of our invention are not disclosed or inferred.

The cyclopropyl carboxylic acid esters of our invention may be prepared by any one of a number of processes. Thus, a preferred process is to react cyclopropyl carboxylic acid having the structure:

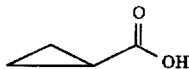

with a hydroxyl derivative according to the reaction:

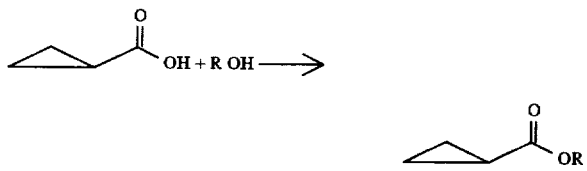

Preferably, this reaction is carried out in the presence of a protonic acid such as paratoluene sulfonic acid.

The reaction is carried out at reflux conditions, for example, between about 110° and 130° C. at atmospheric pressure while simultaneously azeotropically removing the water of reaction. The reaction time varies between about 1 hour and about 5 hours. At the end of the reaction, the reaction mass is washed with water and is then neutralized with, for example, 10% aqueous sodium bicarbonate. The organic phase is separated from the aqueous phase and the organic phase is dried over anhydrous magnesium sulfate and then fractionally distilled, for example, on a 12 inch Goodloe packed column. Alternatively, the cyclopropyl carboxylic acid esters of our invention may be prepared according to other esterification reactions well known to those skilled in the art, for example, those disclosed in U.S. Pat. No. 3,925,460 issued on Dec. 9, 1975, the specification for which is incorporated by reference herein.

Table I below sets forth the cyclopropyl carboxylic acid esters of our invention and their fragrance properties:

TABLE I

| Structure of Compound | Perfumery Property |
|---|---|
| The compound having the structure:<br><br>prepared according to Example I, bulked distillation fractions 8–22. | An intense, long lasting herbaceous, "rain forest", green, onion, garlic aroma. |
| The compound having the structure:<br><br>prepared according to Example II, bulked distillation fractions 7–11. | An almond, anisic, cherry, apple and pear aroma with apple, almond, cherry, anisic, hyacinth and lilac topnotes. |
| The compound having the structure:<br><br>prepared according to Example III, bulked distillation fractions 8–13. | A fruity, woody, mahogany, cigar box aroma with intense woody, fruity and amber topnotes. |
| The compound having the structure:<br><br>prepared according Example IV, bulked distillation fractions 6–10. | An intense fruity, green and woody aroma with woody, green and fruity topnotes. |

One or more of the cyclopropyl carboxylic acid esters of our invention prepared in accordance with the processes set forth, supra, and described in detail in the Examples, infra, and one or more auxiliary perfume ingredients including, for example, alcohols, aldehydes, ketones, terpenic hydrocarbons, nitriles, esters other than the cyclopropyl carboxylic acid esters of our invention, lactones, ethers, natural essential oils and synthetic essential oils may be admixed so that the combined odors of the individual components produce a pleasant and desired fragrance, particularly and preferably in the woody cologne and muguet fragrances. Such compositions usually contain:

(a) the main note or the "bouquet" or foundation stone of the invention;

(b) modifiers which round off and accompany the main note;

(c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute their particular olfactory characteristics, however, the overall sensory effect of the perfume composition will be at least the sum total of the effects of each of the ingredients. Thus, the cyclopropyl carboxylic acid esters of our invention can be used to alter, modify or enhance the aroma characteristics of a perfume composition, for example, by utilizing or moderating the olfactory reaction contributed by another ingredient in the composition.

The amount of one or more of the cyclopropyl carboxylic acid esters of our invention which will be effective in perfume compositions as well as in perfumed articles (e.g., anionic, cationic, nonionic or zwitterionic detergents, soaps, Fabric softener compositions, fabric softener articles and perfumed polymers) and colognes depends upon many factors including the other ingredients, their amounts and the effects which are desired. It has been found that perfume compositions containing as little as 0.01% of one or more of the cyclopropyl carboxylic acid esters of our invention or even less (e.g., 0.005%) can be used to impart, augment or enhance strong and persistent herbaceous, "rain forest", green, onion, garlic, almond, anisic, fruity, cherry, apple, pear, woody, mahogany and cigar box aromas with green, fruity, apple, almond, cherry, anisic, lilac, hyacinth, woody and amber topnotes to soaps, cosmetics, anionic, cationic, nonionic or zwitterionic detergents, fabric softener articles, microporous polymers, particularly acrylic resins, polyethylenes and other products. The amount employed can range up to 70% of the fragrance components and will depend on considerations of cost, nature of the end product, the effect desired on the finished product and the particular fragrance sought.

The cyclopropyl carboxylic acid esters of our invention prepared in accordance with the processes as set forth, supra (taken alone or taken together with other ingredients in perfume compositions) is (are) useful as (an) olfactory component(s) in detergents and soaps, space odorants and deodorants, perfumes, colognes, toilet waters, bath preparations such as creams, deodorants, hand lotions and sun screens; powders, such as talcs, dusting powders, face powders, microporous "perfumed" slow release polymers and the like.

When used as (an) olfactory component(s) in perfumed articles, as little as 0.005% of one or more of the cyclopropyl carboxylic acid esters of our invention will suffice to impart, augment or enhance strong, persistent herbaceous, "rain forest", green, onion, garlic, almond, anisic, fruity, cherry, apple, pear, woody, mahogany and cigar box aromas with green, fruity, apple, almond, cherry, anisic, lilac, hyacinth, woody and amber topnotes. Generally, no more than 6% of at least one of the cyclopropyl carboxylic acid esters of our invention based on the ultimate end product is required in the perfumed article. Accordingly, the range of use of at least one of the cyclopropyl carboxylic acid esters of our invention in perfumed articles, per se, is from about 0.005% up to about 6% by weight based on the perfumed article.

In addition, the perfume composition or fragrance composition of our invention can contain a vehicle or carrier for one or more of the cyclopropyl carboxylic acid esters of our invention. The vehicle can be a liquid such as a non-toxic alcohol, e.g., ethyl alcohol, a non-toxic glycol, e.g., propylene glycol or the like. The carrier can be an absorbent solid such as a gum (e.g., gum arabic, guar gum or xanthan gum or combinations thereof) or components for encapsulating the composition (such as by coacervation) or using prepolymers such as urea-formaldehyde prepolymers which are able to form a urea-formaldehyde polymer capsule around a liquid perfume center.

It will thus be apparent that the cyclopropyl carboxylic acid esters of our invention can be utilized to alter, modify or enhance sensory properties particularly organoleptic properties such as fragrances of a wide variety of consumable materials.

The following Examples I–IV, inclusive, set forth means for preparing the cyclopropyl carboxylic acid esters of our invention. The examples including and following Example V, infra, set forth illustrations of organoleptic utilities of the cyclopropyl carboxylic acid esters of our invention.

All parts and percentages given herein are by weight unless otherwise specified.

EXAMPLE I

Preparation of the Cis-3-Hexenyl Ester of Cyclopropans Carboxylic Acid

Reaction:

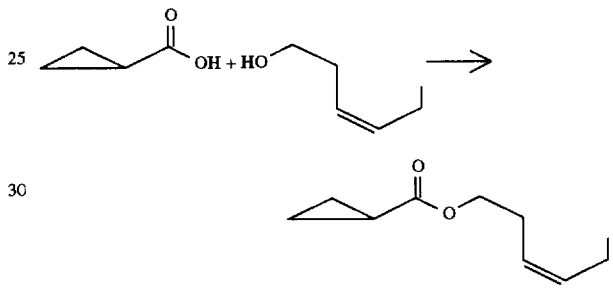

Into a 2 liter, three-neck reaction flask equipped with a Bidwell trap, mechanical stirrer with Teflon blade, Thermowell with thermocouple, reflux condenser and heating mantle are placed the following materials:

cyclopropane carboxylic acid having the structure:

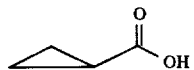

. . . 284 (3.3 moles);

cis-3-hexenol . . . 300 grams (3.0 moles);

paratoluene sulfonic acid . . . 5.7 grams; and toluene . . . 240 ml.

The reaction mass with stirring is heated to reflux temperature at atmospheric pressure (116° C.) and azeotropic removal of water via the Bidwell trap is begun.

Azeotropic removal of water is continued until the pot temperature of the reaction mass is 140° C. A total of 55 grams of water (3.05 moles) is removed.

The reaction mass is then cooled to room temperature and the reaction mixture weighing 738 grams and having a pH of 3 is washed with 370 grams of warm (45° C.) water. The resulting product now exists in two phases: an aqueous phase and an organic phase. The aqueous phase is separated from the organic phase and is discarded. The organic phase is then washed with 500 grams of 10% aqueous sodium bicarbonate solution. The organic phase is then separated from the aqueous phase and the organic phase, weighing 709 grams and having a pH of 7.5 is fractionally distilled on a Goodloe column yielding the following fractions:

| Fraction Number | Vapor Temperature (°C.) | Liquid Temperature (°C.) | Vacuum mm/Hg. Pressure | Reflux Ratio | Weight of Fraction | % Product |
|---|---|---|---|---|---|---|
| 1 | 23/88 | 23/80 | 3 | 1/9 | 150 | solvent |
| 2 | 92 | 92 | 1 | 9/1 | 11 | 75 |
| 3 | 83 | 88 | 1 | 9/1 | 16 | 89 |
| 4 | 78 | 89 | 1 | 9/1 | 17 | 99 |
| 5 | 78 | 90 | 1 | 9/1 | 14 | 99 |
| 6 | 79 | 90 | 1 | 9/1 | 16 | 99 |
| 7 | 81 | 90 | 1 | 9/1 | 15 | 99 |
| 8 | 82 | 90 | 1 | 9/1 | 16 | 99 |
| 9 | 81 | 90 | 1 | 1/1 | 21 | 99 |
| 10 | 82 | 90 | 1 | 1/1 | 20 | 99 |
| 11 | 81 | 90 | 1 | 1/1 | 17 | 99 |
| 12 | 87 | 90 | 1 | 1/1 | 22 | 99 |
| 13 | 83 | 90 | 1 | 1/1 | 20 | 99 |
| 14 | 82 | 90 | 1 | 1/1 | 22 | 99 |
| 15 | 82 | 89 | 1 | 1/1 | 22 | 99 |
| 16 | 82 | 89 | 1 | 1/1 | 22 | 99 |
| 17 | 83 | 89 | 1 | 1/1 | 26 | 99 |
| 18 | 84 | 90 | 1 | 1/1 | 20 | 99 |
| 19 | 83 | 89 | 1 | 1/1 | 20 | 99 |
| 20 | 85 | 90 | 1 | 1/4 | 25 | 99 |
| 21 | 87 | 90 | 1 | 1/4 | 29 | 99 |
| 22 | 88 | 97 | 1 | 1/4 | 28 | 99 |
| 23 | 87 | 99 | 1 | 1/4 | 28 | 99 |
| 24 | 88 | 111 | 1 | 1/4 | 19 | 99 |

A total of 461 grams of product was obtained from the distillation which represents a chemical yield of 91%. Fractions 8–22 are bulked. Bulked distillation Fractions 8–22 have an intense, long lasting, herbaceous, "rain forest", green, onion and garlic aroma. Bulked fractions 8–22 consist of the compound having the structure:

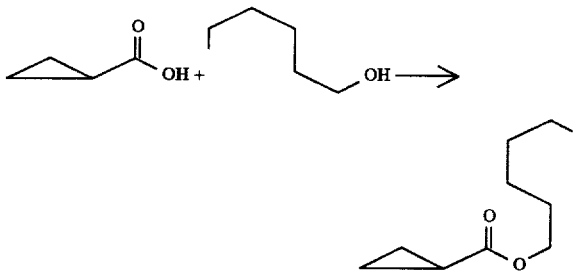

as confirmed by GLC, NMR, mass spectral and IR analyses.

EXAMPLE II

Preparation of n-Hexyl Ester of Cyclopropane Carboxylic Acid

Reaction:

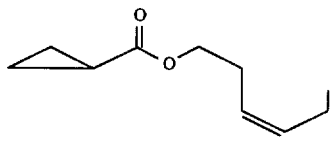

Into a 1 liter, three-neck flask equipped with a Bidwell trap, stirrer, heating mantle and reflux condenser are placed the following materials:

propane carboxylic acid . . . 100 grams;
n-Hexanol . . . 150 grams;
toluene . . . 250 ml; and
paratoluene sulfonic acid . . . 65 grams.

The reaction mass is heated to reflux and water is azeotropically removed therefrom. After 3 hours, the reaction mass is cooled to room temperature and the resulting product is admixed with an equal volume of 10% aqueous sodium bicarbonate.

The aqueous phase is separated from the organic phase and the organic phase is dried over anhydrous magnesium sulfate and fractionally distilled, yielding the following fractions:

| Fraction Number | Vapor Temperature (°C.) | Liquid Temperature (°C.) | Vacuum mm/Hg. Pressure |
|---|---|---|---|
| 1 | 22/35 | 22/57 | 1.8 |
| 2 | 86 | 110 | 1.4 |
| 3 | 102 | 111 | 1.4 |
| 4 | 112 | 112 | 1.3 |
| 5 | 112 | 112 | 1.3 |
| 6 | 112 | 112 | 1.3 |
| 7 | 97 | 112 | 1.2 |
| 8 | 89 | 95 | 1.0 |
| 9 | 82 | 96 | 1.0 |
| 10 | 89 | 102 | 1.0 |
| 11 | 89 | 180 | 1.0 |
| 12 | 89 | 180 | 0.7 |

Distillation fractions 7–11 are bulked.
The resulting product has the structure:

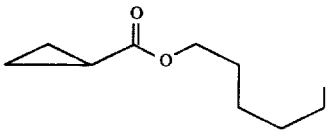

as confirmed by NMR, IR, GLC and mass spectral analyses. The resulting product, bulked distillation fractions 7–11, has an almond, anisic, cherry, apple and pear aroma with apple, almond, cherry, anisic, hyacinth and lilac topnotes.

EXAMPLE III

Preparation of n-Heptyl Ester of Cyclopropane Carboxylic Acid

Reaction:

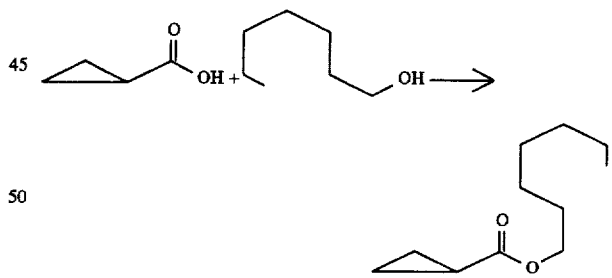

Into a 1 liter reaction vessel equipped with stirrer, thermometer, reflux condenser, heating mantle and Bidwell trap are placed the following materials:

n-heptanol . . . 174 grams;
cyclopropane carboxylic acid . . . 215 grams;
toluene . . . 150 ml; and
paratoluene sulfonic acid . . . 0.70 grams.

With stirring, the reaction mass is heated to reflux and maintained at reflux for a period of 3 hours while water is azeotropically removed by means of the Bidwell trap.

At the end of the 3 hour period, the reaction mass is cooled to room temperature. The resulting product is then admixed with an equal volume of 5% aqueous sodium bicarbonate solution. The organic phase is separated from the aqueous phase and the organic phase is then admixed with an equal volume of water.

The organic phase is separated from the aqueous phase and the organic phase is then dried over anhydrous magnesium sulfate. The resulting product is then fractionally distilled, yielding the following fractions:

| Fraction Number | Vapor Temperature (°C.) | Liquid Temperature (°C.) | Vacuum mm/Hg. Pressure | Reflux Ratio |
|---|---|---|---|---|
| 1 | 21/64 | 23/90 | 1.9 | 4/1 |
| 2 | 63 | 98 | 0.8 | 4/1 |
| 3 | 90 | 106 | 1.0 | 4/1 |
| 4 | 93 | 105 | 1.0 | 4/1 |
| 5 | 100 | 110 | 1.0 | 4/1 |
| 6 | 93 | 117 | 1.0 | 4/1 |
| 7 | 99 | 110 | 1.0 | 4/1 |
| 8 | 93 | 107 | 1.0 | 4/1 |
| 9 | 92 | 108 | 1.0 | 4/1 |
| 10 | 92 | 107 | 1.0 | 4/1 |
| 11 | 90 | 106 | 1.0 | 4/1 |
| 12 | 98 | 108 | 1.0 | 4/1 |
| 13 | 95 | 105 | 1.0 | 4/1 |
| 14 | 87 | 105 | 1.0 | 4/1 |

Fractions 8–13 are bulked. Bulked distillation fractions 8–13 consist of the compound having the structure:

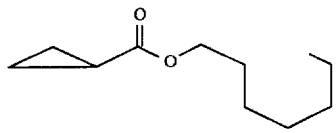

as confirmed by NMR, IR, mass spectral and GLC analyses. The compound having the structure:

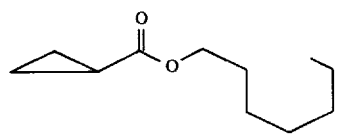

has a fruity, woody, mahogany and cigar box aroma with intense, woody, fruity and amber topnotes.

EXAMPLE IV

Preparation of the Cyclohexyl Methyl Ester of Cyclopropane Carboxylic Acid

Reaction:

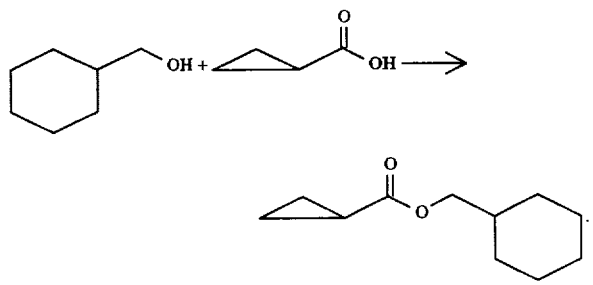

Into a 1 liter reaction vessel equipped with stirrer, thermometer, reflux condenser, heating mantle and Bidwell trap are placed the following materials:

cyclopropane carboxylic acid . . . 136 grams;
sulfuric acid (93%) . . . 7 ml;
cyclohexyl methanol . . . 150 grams; and
toluene . . . 150 ml.

The reaction mass is heated to reflux with stirring and refluxed at atmospheric pressure for a period of 1.5 hours, while removing water azeotropically via the Bidwell trap. At the end of the 1.5 hour period, the reaction mass is cooled to room temperature.

The reaction mass is then washed with an equal volume of water. The aqueous phase is separated from the organic phase and the organic phase is washed with an equal volume of saturated sodium carbonate solution.

The aqueous phase is separated from the organic phase and the organic phase is then dried over anhydrous magnesium sulfate.

The resulting product is then fractionally distilled, yielding the following fractions:

| Fraction Number | Vapor Temperature (°C.) | Liquid Temperature (°C.) | Vacuum mm/Hg. Pressure | Reflux Ratio |
|---|---|---|---|---|
| 1 | 33 | 84 | 6.0 | 100 |
| 2 | 111 | 117 | 0.8 | 100 |
| 3 | 104 | 108 | 0.7 | 9/1 |
| 4 | 104 | 108 | 0.7 | 9/1 |
| 5 | 104 | 109 | 0.7 | 9/1 |
| 6 | 104 | 109 | 0.7 | 9/1 |
| 7 | 105 | 110 | 0.7 | 9/1 |
| 8 | 105 | 110 | 0.7 | 9/1 |
| 9 | 104 | 115 | 0.7 | 9/1 |
| 10 | 105 | 114 | 0.7 | 9/1 |
| 11 | 92 | 121 | 0.5 | 9/1 |
| 12 | 86 | 125 | 0.4 | 9/1 |

Fractions 6–10 are bulked. Bulked distillation fractions 6–10 consist of the compound having the structure:

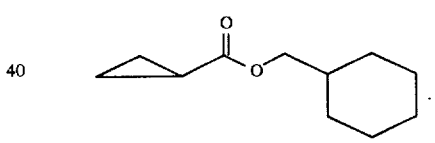

as confirmed by NMR, IRS mass spectral and GLC analyses.

EXAMPLE V

Perfume Formulations

The following woody cologne perfume formulations are prepared:

| Ingredients | Parts by Weight | | | |
|---|---|---|---|---|
| | V(A) | V(B) | V(C) | V(D) |
| Bergamot oil | 150 | 150 | 150 | 150 |
| Orange oil | 200 | 200 | 200 | 200 |
| Lemon oil | 50 | 50 | 50 | 50 |
| Eugenol | 10 | 10 | 10 | 10 |
| 4-(4-methyl-4-hydroxyamyl)-Δ³cyclohexane carboxaldehyde (LYRAL ®, Trademark of International Flavors & Fragrances Inc. of New York, New York) | 40 | 40 | 40 | 40 |
| Ylang oil | 2 | 2 | 2 | 2 |
| Petigrain Paraguay | 10 | 10 | 10 | 10 |
| γ-Methyl ionone | 20 | 20 | 20 | 20 |
| Vetiver Venezuela | 18 | 18 | 18 | 18 |

-continued

| Ingredients | Parts by Weight | | | |
|---|---|---|---|---|
| | V(A) | V(B) | V(C) | V(D) |
| 3-α-Methyl-dodecahydro-6,6,9a-trimethyl-napthol[2.1-b]furan | 5 | 5 | 5 | 5 |
| Product produced by the reaction of acetic anhydride, polyphosphoric acid and 1,5,9-trimethyl cyclododecatriene-1,5,9 according to the process of Example I of U.S. Pat. No. 3,718,698, the specification for which is incorporated by reference herein. | 50 | 50 | 50 | 50 |
| Octahydro-9,9-dimethyl-1,6-methano-naphthalene-1-[2H]-ol produced according to Example III of U.S. Pat. No. 3,996,169, the specification for which is incorporated by reference herein. | 50 | 50 | 50 | 50 |
| The compound having the structure: | 25 | 0 | 0 | 0 | prepared according to Example I, supra, bulked distillation fractions 8–22.

| The compound having the structure: | 0 | 25 | 0 | 0 |
|---|---|---|---|---| prepared according to Example II, supra, bulked distillation fractions 7–11.

| The compound having the structure: | 0 | 0 | 25 | 0 |
|---|---|---|---|---| prepared according to Example III, supra, bulked distillation fractions 8–13.

| The compound having the structure: | 0 | 0 | 0 | 25 |
|---|---|---|---|---|

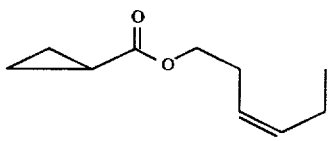

prepared according to Example IV, supra, bulked distillation fractions 6–10.

The compound having the structure:

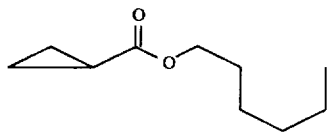

prepared according to Example I, bulked distillation fractions 8–22, imparts to this woody cologne formulation strong, persistent herbaceous, "rain forest", green, onion and garlic undertones. Accordingly, the perfume composition of Example V(A) is described as:

"a woody cologne aroma with strong, persistent herbaceous, "rain forest", green, onion and garlic undertones".

The compound having the structure:

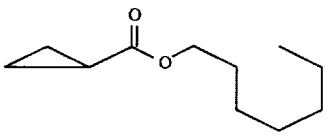

prepared according to Example II, bulked distillation fractions 7–11, imparts to this woody cologne formulation strong, persistent almond, anisic, cherry, apple and pear undertones with apple, almond, cherry, anisic, hyacinth and lilac topnotes. Accordingly, the perfume composition of Example V(B) can be described as:

"a woody cologne aroma with strong, persistent almond, anisic, cherry, apple and pear undertones with apple, almond, cherry, anisic, hyacinth and lilac topnotes".

The compound having the structure:

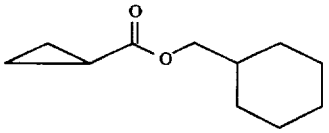

prepared according to Example III, bulked distillation fractions 8–13, imparts to this woody cologne formulation strong, persistent fruity, woody, mahogany and cigar box undertones with woody, fruity and amber topnotes. Accordingly, the perfume composition of Example V(C) can be described as:

"a woody cologne aroma with strong, persistent fruity, woody, mahogany and cigar box undertones with woody, fruity and amber topnotes".

The compound having the structure:

prepared according to Example IV, bulked distillation fractions 6–10, imparts to this woody cologne formulation strong, persistent fruity, green and woody undertones with woody, green and fruity topnotes. Accordingly, the perfume composition of Example V(D) can be described as:

"a woody cologne aroma with strong, persistent fruity, green and woody undertones with woody, green and fruity topnotes".

EXAMPLE VI

Preparation of Cosmetic Powder Composition

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure: 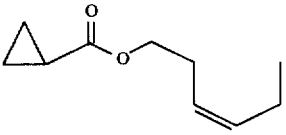<br><br>prepared according to Example I, supra, bulked distillation fractions 8–22. | An intense, long lasting, herbaceous, "rain forest", green, onion and garlic aroma. |
| The compound having the structure: 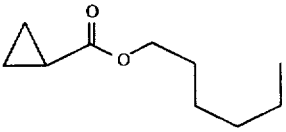<br><br>prepared according Example II, bulked distillation fractions 7–11. | An almond, anisic, cherry, apple and pear aroma with apple, almond, cherry, anisic, hyacinth and lilac topnotes. |
| The compound having the structure: 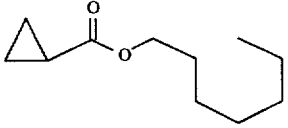<br><br>prepared according to Example III, bulked distillation fractions 8–13. | A fruity, woody, mahogany and cigar box aroma with intense woody, fruity and amber topnotes. |
| The compound having the structure: 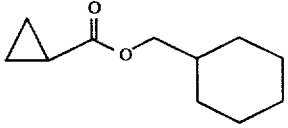<br><br>prepared according to Example IV, bulked distillation fractions 6–10. | An intense, fruity, green and woody aroma with woody, green fruity topnotes. |
| The perfume composition of Example V(A). | A woody cologne aroma with strong, persistent herbaceous, "rain forest", green, onion and garlic undertones. |
| The perfume composition of Example V(B). | A woody cologne aroma with strong, persistent almond, anisic, cherry, apple and pear undertones with apple, almond, cherry, anisic, hyacinth and lilac topnotes. |
| The perfume composition of Example V(C). | A woody cologne aroma with strong, persistent fruity, woody, mahogany and cigar box undertones with woody, fruity and amber topnotes. |
| The perfume composition of Example V(D). | A woody cologne aroma with strong, persistent fruity, green and woody undertones with woody, green and fruity topnotes. |

EXAMPLE VII

Perfumed Liquid Detergents

Concentrated liquid detergents (Lysine salt of n-dodecybenzene sulfonic acid as more specifically described in U.S. Pat. No. 3,948,818 issued on Apr. 6, 1976 incorporated by reference herein) with aroma nuances as set forth in Table II of Example VI are prepared containing 0.10%, 0.15%, 0.20%, 0.25%, 0.30% and 0.35% of the substance set forth in Table II of Example VI. They are prepared by adding and homogeneously mixing the appropriate quantity of substance set forth in Table II of Example VI in the liquid detergent. The detergents all possess excellent aromas as set forth in Table II of Example VI, the intensity increasing with greater concentrations of substances as set forth in Table II of Example VI.

EXAMPLE VIII

Preparation of Cologne and Handkerchief Perfumes

Compositions as set forth in Table II of Example VI are incorporated into colognes at concentrations of 2.0%, 2.5%, 3.0%, 3.5%, 4.0% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example VI are imparted to the colognes and to the handkerchief perfumes at all levels indicated.

EXAMPLE IX

Preparation of Soap Composition

100 Grams of soap chips [per sample] (IVORY® produced by the Procter & Gamble Company of Cincinnati, Ohio) are each mixed with 1 gram samples of substances as set forth in Table II of Example VI until homogeneous compositions are obtained. In each of the cases, the homogeneous compositions are heated under 8 atmospheres pressure at 180° C. for a period of 3 hours and the resulting liquids are placed into soap molds. The resulting soap cakes, on cooling, manifest aromas as set forth in Table II of Example VI.

EXAMPLE X

Preparation of Solid Detergent Compositions

Detergents are prepared using the following ingredients according to Example I of Canadian Patent No. 1,007,948 (incorporated by reference herein):

| Ingredients | Percent by Weight |
|---|---|
| NEODOL ® 45-11 (a $C_{12}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example VI. Each of the detergent samples has an excellent aroma as indicated in Table II of Example VI.

EXAMPLE XI

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and their perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57% $C_{20-22}$ HAPS;
   22% isopropyl alcohol;
   20% antistatic agent; and
   1% of one of the substances as set forth in Table II of Example VI, supra.

Fabric softening compositions prepared according to Example I at column 15 of U.S. Pat. No. 3,632,396 having the aroma characteristics as set forth in Table II of Example VI, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example VI is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added softener non-woven fabrics and these aroma characteristics are described in Table II of Example VI, supra.

EXAMPLE XII

Hair Spray Formulations

The following hair spray formulation is prepared by first dissolving PVP/VA E-735 copolymer manufactured by the GAF Corporation of 140 West 51st Street, New York, N.Y. in 91.62 grams of 95% of food grade ethanol. 8.0 Grams of the polymer is dissolved in the alcohol. The following ingredients are added to the PVP/VA alcoholic solution:

| Ingredients | Percent by Weight |
| --- | --- |
| Dioctyl sebacate | 0.05 |
| Benzyl alcohol | 0.10 |
| Dow Corning 473 fluid (prepared by the Dow Corning Corporation) | 0.10 |
| TWEEN ® 20 surfactant (prepared by ICI America Corporation) | 0.03 |
| One of the perfumery substances as set forth in Table II of Example VI, supra | 0.10 |

The perfuming substances as set forth in Table II of Example VI add aroma characteristics as set forth in Table II of Example VI which are rather intense and aesthetically pleasing to the users of the soft-feel, good-hold pump hair sprays.

EXAMPLE XIII

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of the Union Carbide Corporation) (1.4 weight percent). The resulting melt is admixed with Stepanol WAT produced by the Stephan Chemical Company (35.0 weight percent). The resulting mixture is heated to 60° C. and mixed until a clear solution is obtained (at 60° C.). This material is "COMPOSITION A".

GAFQUAT® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by the Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table II of Example VI is added to the mixture. The resulting mixture is cooled to 40° C. and blending is carried out for an additional one hour in each case. At the end of this blending period, the resulting material has a pleasant fragrance as indicated in Table II of Example VI.

What is claimed is:

1. A process for augmenting, enhancing or imparting an aroma in or to a consumable material selected from the group consisting of perfume compositions, perfumed articles and colognes comprising the step of intimately admixing with said consumable material an aroma augmenting, enhancing or imparting quantity and concentration of at least one cyclopropyl carboxylic acid ester defined according to the structure:

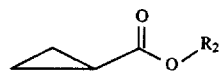

wherein $R_2$ is selected from the group consisting of n-hexyl, cis-3-hexenyl, cyclohexyl methyl and n-heptyl.

2. The process of claim 1 wherein $R_2$ is n-hexyl.

3. The process of claim 1 wherein $R_2$ is cis-3-hexenyl.

4. The process of claim 1 wherein $R_2$ is cyclohexyl methyl.

5. The process of claim 1 wherein $R_2$ is n-heptyl.

6. A consumable material selected from the group consisting of perfume compositions, perfumed articles and colognes comprising a consumable material base and intimately admixed therewith an aroma augmenting, enhancing or imparting quantity and concentration of at least one cyclopropyl carboxylic acid esters defined according to the structure:

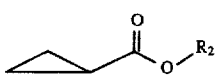

wherein $R_2$ is selected from the group consisting of n-hexyl, cis-3-hexenyl, cyclohexyl methyl and n-heptyl.

7. The consumable material of claim 6 wherein the consumable material is a perfume composition.

8. The consumable material of claim 6 wherein the consumable material is a perfumed article.

9. The consumable material of claim 6 wherein the consumable material is a cologne consisting of water, alcohol and an aroma augmenting, enhancing or imparting quantity and concentration of a compound defined according to the structure:

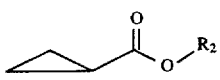

wherein R₂ is selected from the group consisting of n-hexyl, cis-3-hexenyl, cyclohexyl methyl and n-heptyl.

10. The consumable material of claim 6 wherein the consumable material is a perfumed microporous polymer and the compound defined according to the structure:

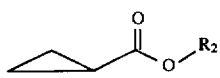

is contained within the interstices of said microporous polymer.

11. The compound having the structure:

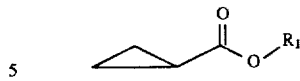

wherein R₁ is selected from the group consisting of cis-3-hexenyl and cyclohexyl methyl.

12. The compound of claim 11 wherein R₁ is cis-3-hexenyl.

13. The compound of claim 11 wherein R₁ is cyclohexyl methyl.

14. A consumable material which is a perfumed microporous polymer containing in the interstices thereof at least one compound defined according to claim 11.

* * * * *